US00PP24008P3

(12) United States Plant Patent
Fransen

(10) Patent No.: US PP24,008 P3
(45) Date of Patent: Oct. 29, 2013

(54) ***HOSTA* PLANT NAMED 'VOLCANO ISLAND'**

(50) Latin Name: ***Hosta* hybrid**
Varietal Denomination: Volcano Island

(75) Inventor: Marco Fransen, Tel Aar (NL)

(73) Assignee: Venooij V.O.F. (NL)

( * ) Notice: Subject to any disclaimer, the term of this patent is extended or adjusted under 35 U.S.C. 154(b) by 18 days.

(21) Appl. No.: 13/135,823

(22) Filed: Jul. 14, 2011

(65) Prior Publication Data

US 2013/0019362 P1 Jan. 17, 2013

(51) Int. Cl.
*A01H 5/00* (2006.01)

(52) U.S. Cl.
USPC ..... Plt./353

(58) Field of Classification Search
USPC ..... Plt./353
See application file for complete search history.

(56) References Cited

PUBLICATIONS

*Hosta* 'Volcano Island' In the Country 2013 catalog, retrieved on Dec. 6, 2012. Retrieved from the Internet at <http://www.inthecountrygardenandgifts.com/catalog/index.php?main_page=product_info&cPath=1_12&products_id=883> 2pp.*

* cited by examiner

*Primary Examiner* — June Hwu
(74) *Attorney, Agent, or Firm* — Cassandra Bright

(57) ABSTRACT

A new and distinct *Hosta* cultivar named 'Volcano Island' is disclosed, characterized by distinctive large, bright foliage with a green margin, vigorous plant habit and strong foliage, with good resistance to environmental stressors. The new variety is a *Hosta*, typically used for outdoor ornamental purposes.

2 Drawing Sheets

Latin name of the genus and species: *Hosta* hybrid.
Variety denomination: 'VOLCANO ISLAND'.

BACKGROUND OF THE INVENTION

The new cultivar was discovered as an induced mutation using the known chemical colchicine, of *Hosta* hybrid 'Paradise Island' U.S. Plant Pat. No. 20,798. 'Volcano Island' was discovered by the inventor, Marco Fransen, a citizen of the Netherlands in October of 2008, at a research facility in Ter Aar, The Netherlands. The intent of the breeding program was to create new tetraploid *Hosta* hyrids with stronger characteristics.

Directly after discovery of the tetraploid mutation, the inventor initiated cultivation in tissue culture, during October of 2008, in a commercial laboratory in Iribov Heerhugowaard, the Netherlands. Subsequently 'Volcano Island' has been reproduced by micro-propagation in a commercial laboratory in Iribov Heerhugowaard, the Netherlands and has shown that the unique features of this cultivar are stable and reproduced true to type through several generations.

SUMMARY OF THE INVENTION

The cultivar 'Volcano Island' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Volcano Island' These characteristics in combination distinguish 'Volcano Island' as a new and distinct *Hosta* cultivar:

1. Distinctive, bright foliage with a green margin.
2. Thick foliage resistant to environmental stressors.

3. Large foliage
4. Vigorous plant.

COMPARISON TO PARENT

Plants of the new cultivar 'Volcano Island' are similar to plants of the parent; *Hosta* hybrid 'Paradise Island' in most horticultural characteristics, however, plants of the new cultivar 'Volcano Island' are more vigorous and produce thicker, stronger leaves than the parent variety. Additionally, the new variety produces larger foliage than 'Paradise Island'. Leaves of 'Volcano Island' have a wider variegation on the margin than 'Paradise Island'.

COMMERCIAL COMPARISON

'Volcano Island' can be compared to the commercial variety *Hosta* hybrid 'Eye Declare' U.S. Plant Pat. No. 18,466. The varieties are similar in most horticultural characteristics, however, plants of the new cultivar 'Volcano Island' are more vigorous and produce thicker, stronger leaves than the 'Eye Declare'. Additionally, the new variety produces larger foliage than 'Eye Declare' and have foliage with a wider, darker green margin than 'Eye Declare'.

BRIEF DESCRIPTION OF THE PHOTOGRAPHS

Figure 1:
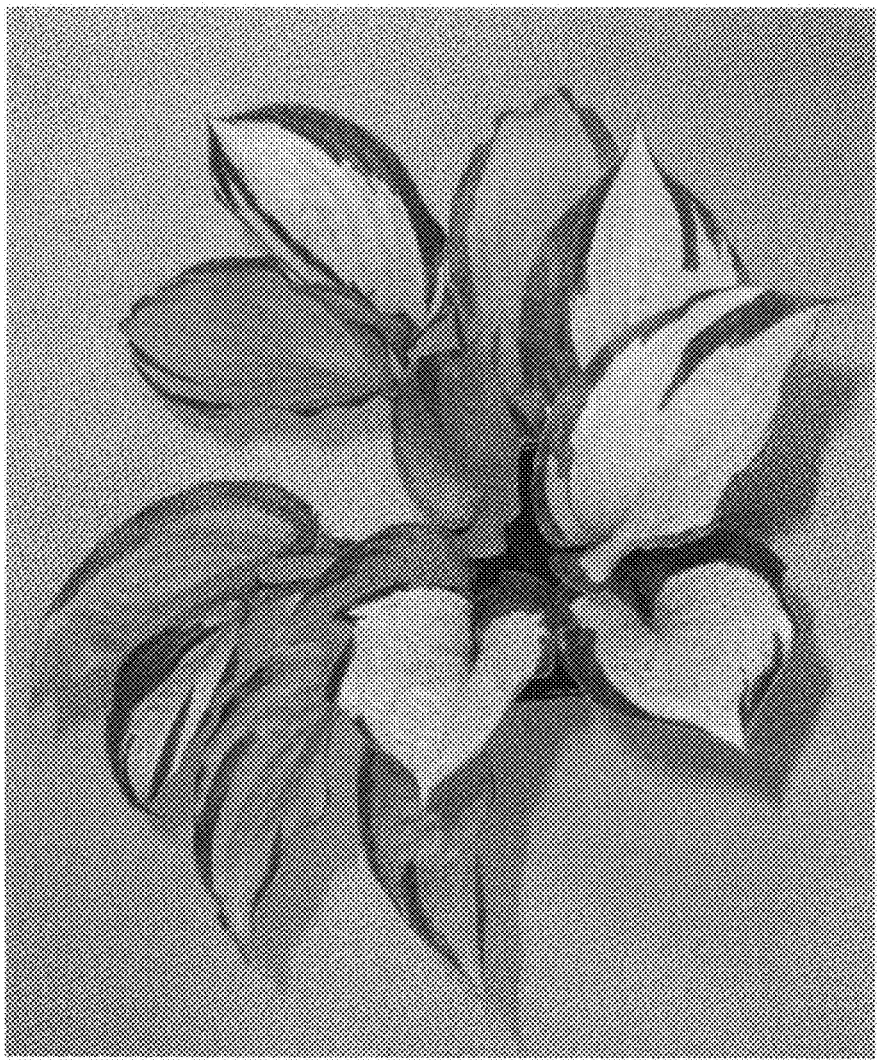

The accompanying photograph in FIG. 1 illustrates in full color a typical plant of 'Volcano Island' grown outdoors. This plant is approximately 6 months old, shown in a 1 liter pot.

Figure 2:
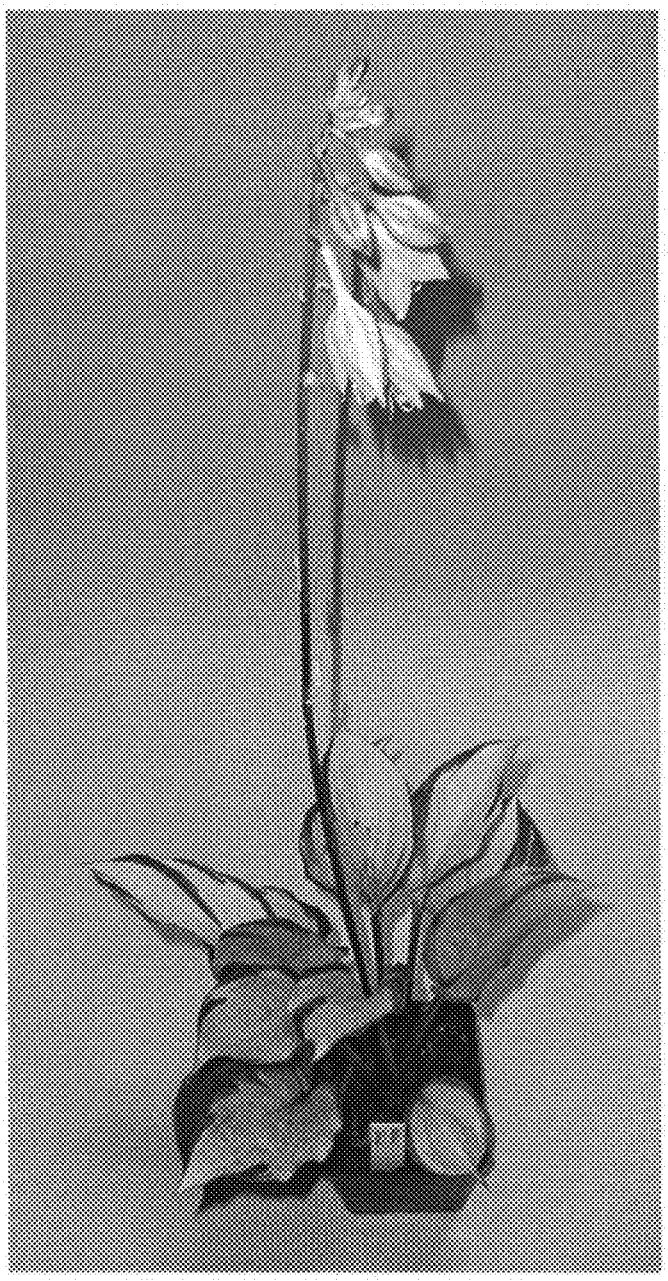

FIG. 2 illustrates a flowering plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007, except where general terms of ordinary dictionary significance are used. The following observations and measurements describe 'Volcano Island' plants grown in a commercial nursery in the Netherlands, from February of 2011 through June of 2011. Temperatures were 5° C. to 20° C. at night and 10° C. to 30° C. during the day. Measurements and numerical values represent averages of typical plant types. No growth regulators or special treatments were used.

Botanical classification: *Hosta* hybrid 'Volcano Island'.

PROPAGATION

Time to initiate roots: Approximately 14 to 21 days at 23° C.

Root description: Fleshy with moderate side roots.

PLANT

Growth habit: Upright, herbaceous perennial plant.

Height: Approximately 35 cm in a 1 liter pot.

Plant spread: Approximately 50 cm.

Growth rate: Moderate.

Branching characteristics: Branches emerge directly from the roots.

Age of plant described: Approximately 4 months from a stage 3 tissue culture.

FOLIAGE

Leaf:

*Quantity per plant*.—Average 30.

*Leaf type*.—Simple, basal emerging.

*Average leaf length*.—Approximately 52 cm.

*Average leaf width*.—Approximately 22 cm, at widest point.

*Apex*.—Acute.

*Base*.—Cordate.

*Overall leaf shape*.—Obovate.

*Overall leaf aspect*.—Arching.

*Margin*.—Slightly undulating.

*Texture of top surface*.—Smooth.

*Texture of bottom surface*.—Smooth.

*Appearance of top surface*.—Slightly leathery.

*Appearance of bottom surface*.—Slightly leathery.

*Pubescence*.—No pubescence on leaves.

*Color*.—Young foliage upper side: Near RHS Yellow-Green 151A, margin near RHS Green 141A. Young foliage under side: Near RHS Yellow-Green 151A, margin near RHS Green 141A. Mature foliage upper side: Near RHS Yellow-Green 154D, margin near RHS Green 141A. Mature foliage under side: Near RHS Yellow-Green 154C, margin near RHS Green 141A.

*Venation*.—Type: Pinnate. Venation coloration upper side: Near RHS Yellow-Green 154D sporadically along central portion of the upper leaf surface. RHS Green 141A sporadically along margin of the upper leaf surface. Venation coloration under side: Near RHS Yellow-Green 154D sporadically along central portion of the under leaf surface. RHS Green 141A sporadically along margin of the under leaf surface.

Leaf petiole:

*Length*.—Approximately 10 cm.

*Width*.—Approximately 2.9 cm at widest point.

*Color*.—Upper side: Near RHS Yellow-Green N144B, heavily flushed Greyed-Purple 184A. Under side: Near RHS Yellow-Green N144C, heavily flushed Greyed-Purple 184A.

*Strength*.—Very strong.

Other foliage characteristics: Thick foliage, resistant to mechanical damage and environmental stressors.

FLOWER

Natural flowering season: Early summer to midsummer.

Inflorescence type and habit: Flowers single, campanulate arranged in racemes.

Rate of flower opening: Lowest flower opens first, all flowers have opened in approx. 2 weeks.

Flower longevity on plant: Approx. 2 weeks.

Quantity of flowers: Average: 25 flowers per raceme.

Raceme size:

*Height*.—Approximately 10.4 cm, from lowest flower to top of Inflorescence.

*Width*.—Approximately 5.5 cm.

Flower:

*Perianth: Arrangement*.—Campanulate.

*Overall flower size*.—Length: Approximately 5.0 cm. Width: Approximately 2.8 cm at widest point.

Color:

*Tepals: When opening*.—:: Outer surface: Violet; near RHS 84A, base purple-violet; near RHS N80C. Inner surface: Purple-violet; near RHS N82B, base purple; near RHS 76A.

*Fully opened*.—Outer surface: Violet; near RHS 84B. Inner surface: Purple-violet; near RHS N82C. Color Changes when Aging: Near RHS 84C.

Sepals or Bracts?:

*Quantity*.—One bract is placed under each individual flower.

*Shape*.—Ovate, concave.

*Length*.—Approximately 2.0 cm.

*Diameter*.—Approximately 0.9 cm.

*Color*.—Outer surface: Yellow-green; near RHS 146D and 151A, tinged greyed-orange; near RHS 177A and purple; near RHS N77C. Inner surface: Yellow-green; near RHS 146D, slightly tinged purple; near RHS N77C. Color Changes when Aging: Greyed-orange; near RHS 177B to 177C.

Bud:

*Shape*.—Obovate.

*Length*.—Approximately 2.7 cm.

*Diameter*.—Approximately 1.0 cm.

*Color*.—Purple-violet; near RHS N82B to N82C, tip slightly darker; near RHS N82A.

Pedicels:

*Length*.—Approximately 0.6 cm.

*Width*.—Approximately 0.2 cm.

*Aspect*.—Placed to the petiole in an average angle of 40° (0°=vertical), curved slightly Downward in an average angle of −40°.

*Color*.—Purple-violet; near RHS N82B to N82C.

Scape:

*Length*.—Approximately 61.8 cm.

*Width*.—Approximately 0.5 cm.

*Angle*.—Near vertical.

*Strength*.—Very strong.

*Color*.—Greyed-purple; near RHS 184A.

Fragrance: No.

REPRODUCTIVE ORGANS

Stamens:

*Number*.—Average 6.

*Filament length*.—Approximately 3.9 cm.

*Filament color*.—Yellow-green; near RHS 145D.

*Anther length*.—Approximately 0.6 cm.

*Anther color*.—Greyed-red; Near RHS 178A.

*Anther shape*.—Oblong, dorsifixed.

*Pollen*.—Moderate, coloured yellow-orange; near RHS 17A.

Pistil:

*Number*.—1.

*Length*.—Approximately 3.9 cm.

*Style color*.—Yellow-green; near RHS 150D.

*Stigma*.—Shape: Club-shaped. Color: Yellow-green; near RHS 150C to 150D.

*Ovary color*.—Yellow-green; near RHS 145A.

OTHER CHARACTERISTICS

Disease resistance: Better resistance to diseases or pests has been observed in this variety, due to the strong, thick foliage.

Temperature tolerance: Hardy perennial, tolerates a temperature range from approximately −30° C. to at least 40° C.

Drought tolerance: No tolerance for drought.

What is claimed is:

1. A new and distinct cultivar of *Hosta* plant named 'Volcano Island' as herein illustrated and described.

* * * * *